(12) United States Patent
Tseng

(10) Patent No.: US 10,309,878 B2
(45) Date of Patent: Jun. 4, 2019

(54) PACKAGING UNIT FOR LIQUID SAMPLE LOADING DEVICES APPLIED IN ELECTRON MICROSCOPE AND PACKAGING METHOD

(71) Applicant: NATIONAL CHENG KUNG UNIVERSITY, Tainan (TW)

(72) Inventor: Shih-Wen Tseng, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 181 days.

(21) Appl. No.: 15/643,493

(22) Filed: Jul. 7, 2017

(65) Prior Publication Data

US 2018/0010988 A1 Jan. 11, 2018

(30) Foreign Application Priority Data

Jul. 7, 2016 (TW) .............................. 105210295 U

(51) Int. Cl.
  *G01N 1/31* (2006.01)
  *H01J 37/20* (2006.01)
  *H01J 37/26* (2006.01)
  *G01N 1/28* (2006.01)

(52) U.S. Cl.
  CPC .............. *G01N 1/312* (2013.01); *H01J 37/20* (2013.01); *H01J 37/261* (2013.01); *G01N 1/2813* (2013.01)

(58) Field of Classification Search
  USPC ...................................................... 73/864.91
  See application file for complete search history.

(56) References Cited

U.S. PATENT DOCUMENTS

| 8,178,851 B2* | 5/2012 | Deshmukh ......... G01N 21/0303 250/311 |
| 8,698,098 B2* | 4/2014 | Deshmukh ............. G01N 21/01 250/440.11 |
| 8,963,102 B2* | 2/2015 | Tsuneta ................... H01J 37/20 250/442.11 |
| 2011/0308336 A1* | 12/2011 | Harmston ................ B01L 9/00 73/864.91 |

FOREIGN PATENT DOCUMENTS

| TW | I275118 B | 3/2007 |
| TW | 200830348 A | 7/2008 |
| TW | 201409011 A | 3/2014 |

\* cited by examiner

*Primary Examiner* — Clayton E. LaBalle
*Assistant Examiner* — Warren K Fenwick
(74) *Attorney, Agent, or Firm* — CKC & Partners Co., LLC

(57) ABSTRACT

The present invention provides a packaging unit for liquid sample loading devices applied in an electron microscope. The liquid sample loading devices may be easily, rapidly, precisely and stably aligned and packaged by an engagement of an upper jig and a bottom jig as well as a first fixing pillar supported in a slide track of the packaging unit. Accordingly, efficiency and a yield of packaging the liquid sample loading devices may be improved. In addition, the packaging unit for the liquid sample loading devices of the present invention may directly package a liquid sample, and thus the liquid sample may maintain its original state.

15 Claims, 6 Drawing Sheets

PACKAGING UNIT FOR LIQUID SAMPLE LOADING DEVICES APPLIED IN ELECTRON MICROSCOPE AND PACKAGING METHOD

RELATED APPLICATIONS

This application claims priority to Taiwan Application Serial Number 105210295, filed Jul. 7, 2016, which is herein incorporated by reference.

BACKGROUND

Field of Invention

The present invention relates to a packaging unit applied in an electron microscope and a packaging method. More particularly, the present invention relates to a packaging unit that may be applied in liquid sample loading devices of the electron microscope and a packaging method.

Description of Related Art

Nowadays, an electron microscope is widely used in detecting samples of various fields. However, a liquid sample needs to be packaged before detected due to its fluidity.

For example, a common method to package the liquid sample is performed by a combination of a semiconductor silicon process and a microelectromechanical technique. Nevertheless, the method can be used only in the liquid sample having high fluidity, and thus the method has lots of limitations. The liquid sample having low fluidity and high viscosity fails to be packaged by the above method due to poor electron transparency and difficulty in imaging under the electron microscope.

When the liquid sample loading devices are packaged by the method in combination of the semiconductor silicon process and the microelectromechanical technique, an upper liquid sample loading device is manually aligned with and adhered to a bottom liquid sample loading device by a human eye using an optical microscope. The method is time-wasting and leads to low yield due to human factors such as stability and manual dexterity.

There is another method that the liquid sample is dried to lower down the fluidity of the liquid sample. However, the drying method may result in problems such as deformation or change in state of the liquid sample, and thus an original state of the liquid sample can't be observed.

Therefore, it is necessary to provide a packaging unit for liquid sample loading devices and a packaging method to easily, rapidly, precisely, stably and directly package the liquid sample, especially for the liquid sample having low fluidity. Accordingly, the liquid sample may maintain its original state.

SUMMARY

Therefore, a purpose of the present invention is providing a packaging unit for liquid sample loading devices applied in an electron microscope. The liquid sample loading devices may be easily, rapidly, precisely and stably aligned and packaged by the package unit.

Another purpose of the present invention is to provide a packaging method using the above package unit.

According to the aforementioned purpose, a packaging unit for liquid sample loading devices applied in an electron microscope is provided. In one embodiment, the packaging unit for the liquid sample loading devices may include an upper jig and a bottom jig. The upper jig may further include a rotating component, a stretchable component and a casing. In which the rotating component may include a first chamber having a first accommodation space and a first opening, and a first internal thread may be disposed in the first chamber. The stretchable component may be disposed in the first accommodation space, and may include a joint piece, a stretchable piece and a first holding element for holding a first liquid sample loading device. The joint piece may have a first external thread matching the first internal thread, so as to movably arrange the stretchable component in the first chamber. The stretchable piece may have one end and the other end oppositely disposed to the end, in which the end is fixed to the joint piece, a portion of the stretchable piece near the other end has a slide track disposed along a longitudinal direction. The first holding element may be fixed to the other end, in which the first holding element and at least one portion of the stretchable piece may protrude from the first opening. The casing may include a second chamber and a first fixing pillar. The second chamber may include a second accommodation space, a second opening and a third opening oppositely disposed to the second opening, in which the rotating component and the stretchable component are disposed in the second accommodation space. A second internal thread is disposed in the third opening, and the first holding element is close to the third opening. The first fixing pillar may be near the third opening and located above the first holding element, in which the first fixing pillar passes through one side of the casing and is slidingly arranged in the slide track. The bottom jig may include a base and a second holding element for holding a second liquid sample loading device, and the second holding element is disposed above the base. In which a second external thread is disposed on an outer wall of the base under the second holding element, and the second internal thread matches the second external thread so that the first holding element and the second holding element may be oppositely disposed.

According to one embodiment of the present invention, the first holding element and the second holding element respectively have a groove to hold the first liquid sample loading device and the second liquid sample loading device thereon.

According to one embodiment of the present invention, the first holding element and the second holding element respectively have an anchor point aligned with the first liquid sample loading device and the second liquid sample loading device.

According to one embodiment of the present invention, the rotating component further includes a fixing trench surrounding the first chamber and disposed on one end of the first chamber far away from the first opening.

According to one embodiment of the present invention, the second opening of the casing comprises a plurality of second fixing pillars, and the second pillars are symmetrically supported on the fixing trench.

According to one embodiment of the present invention, the casing further includes a transparent observing region near the third opening of the casing.

According to one embodiment of the present invention, the rotating component further includes a holder protruding from the second opening.

According to the purposes of the present invention, a packaging method using the above packaging unit is provided. The method includes the following steps: first, a first liquid sample loading device is adhered to a groove of a first holding element. Then, a second liquid sample loading device is adhered to a groove of a second holding element. Next, a liquid sample is added into the first liquid sample loading device or the second liquid sample loading device. Afterwards, an upper jig with a bottom jig is connected by engaging an internal thread of a casing with an external thread of a base. Then, a rotating component is rotated to push out a stretchable component from an accommodation space. Next, the first liquid sample loading device contacts the second liquid sample loading device, thereby adhering the first liquid sample loading device to the second liquid sample loading device.

According to one embodiment of the present invention, before the liquid sample is added, the method further includes applying a small amount of an adhesive to a side of the first liquid sample loading device that is not contacted with the first holding element.

According to one embodiment of the present invention, before the liquid sample is added, the method further includes applying a small amount of the adhesive to a side of the second liquid sample loading device that is not contacted with the second holding element.

According to one embodiment of the present invention, before adhering the first liquid sample loading device to the groove of the first holding element, the method further includes aligning the first liquid sample loading device to an anchor point of the first holding element.

According to one embodiment of the present invention, before adhering the second liquid sample loading device to the groove of the second holding element, the method further comprises aligning the second liquid sample loading device to an anchor point of the second holding element.

According to one embodiment of the present invention, the rotating component is rotated by rotating a holder.

According to one embodiment of the present invention, the stretchable component moves linearly.

According to one embodiment of the present invention, a moving distance of the stretchable component is equal to a length of a slide track.

When the packaging unit for the liquid sample loading devices and the packaging method of the present invention are applied, each element in the upper jig and the bottom jig corresponds to each other. Therefore, the liquid sample loading devices may be easily, rapidly, precisely and stably aligned and packaged, and efficiency and a yield of packaging the liquid sample loading devices may be improved. In addition, the packaging unit for the liquid sample loading devices of the present invention may directly package a liquid sample, and thus the liquid sample may maintain its original state.

BRIEF DESCRIPTION OF THE DRAWINGS

Aspects of the present invention are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The purpose of the present invention is providing a packaging unit for liquid sample loading devices applied in an electron microscope and a packaging method. The liquid sample loading devices may be easily, rapidly, precisely and stably aligned and packaged by an engagement of screw threads of an upper jig and a bottom jig, limited rotation of a stretchable component by a fixing pillar, and a slide track with a specific length of the packaging unit. Therefore, the packaging unit for the liquid sample loading devices and the packaging method of the present invention may directly package a liquid sample, and the liquid sample may maintain its original state. FIG. 1 to FIG. 4 are incorporated to describe the packaging unit for the liquid sample loading devices and the packaging method of the present invention in detailed.

The term of "liquid sample loading device" of the present invention may be referred to a carbon-coated copper grid having a diameter, for example, 3 mm. A hollow portion of the carbon-coated copper grid is covered by a carbon film to hold a sample to be detected. Although the carbon-coated copper grid is illustrated as an example of the liquid sample loading device(s) in the present invention, it is understood by a skilled person in the technical field that the carbon-coated copper grid may be substituted by any other liquid sample loading devices that are common for the electron microscope. Furthermore, a specification of the packaging unit may be adjusted according to a diameter of the liquid sample loading device to be used.

Figure 1:
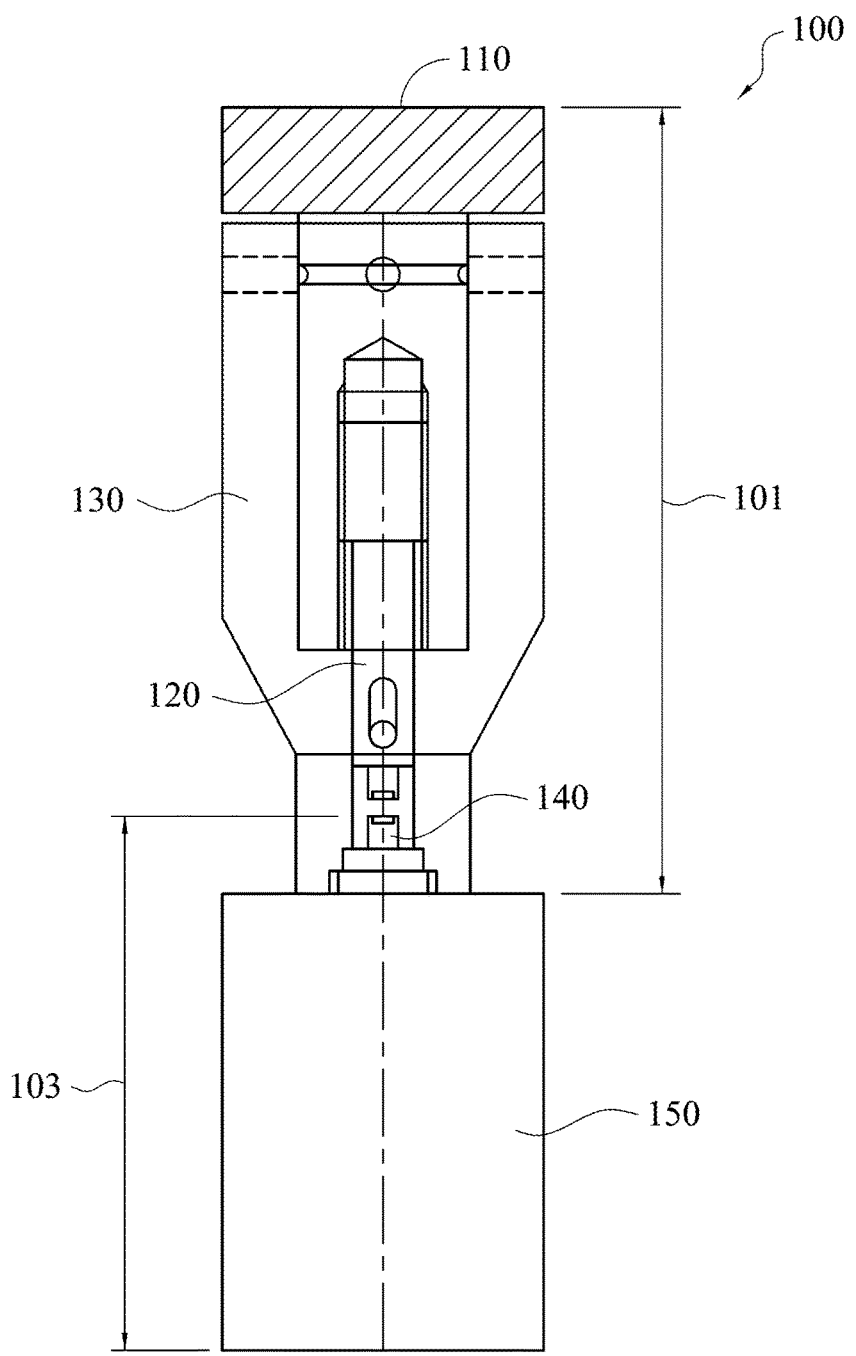
FIG. 1 is a schematic cross-sectional view of a packaging unit for liquid sample loading devices according to one embodiment of the present invention.

Referring to FIG. 1 first, FIG. 1 is a schematic cross-sectional view of a packaging unit for liquid sample loading devices according to one embodiment of the present invention. As shown in FIG. 1, the packaging unit 100 includes an upper jig 101 and a bottom jig 103, in which the upper jig 101 includes a rotating component 110, a stretchable component 120 and a casing 130, and the bottom jig 103 includes a second holding element 140 for holding a second liquid sample loading device (not shown) and a base 150, in which the second holding element 140 is disposed above the base 150.

Figure 2A:
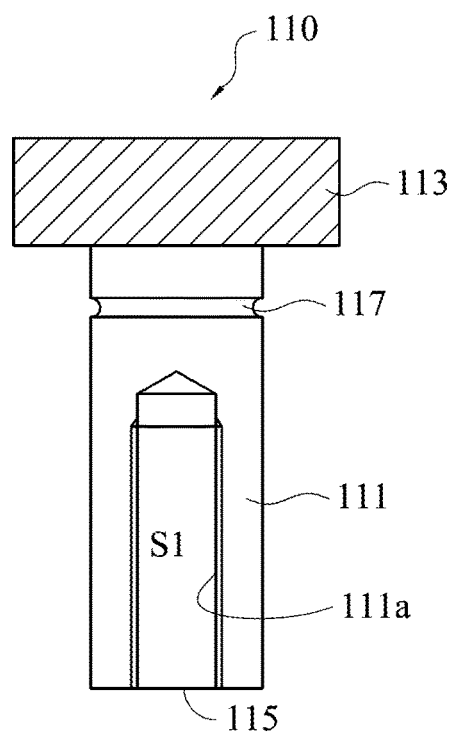
FIG. 2A is a schematic cross-sectional view of a rotating component of a packaging unit for liquid sample loading devices according to one embodiment of the present invention.

FIG. 2A to FIG. 2D further describe detailed structures of every element of the upper jig 101. Referring to FIG. 2A, FIG. 2A is a schematic cross-sectional view of a rotating component of a packaging unit for liquid sample loading devices according to one embodiment of the present invention. As shown in FIG. 2A, the rotating component 110 includes a first chamber 111 and a holder 113, in which the first chamber 111 has a first accommodation space S1 and a first opening 115, and a first internal thread (not shown) is disposed in the first chamber 111. In one embodiment, the internal thread may be, for example, disposed on a sidewall 111a of the first chamber 111. In other embodiments, the rotating component 110 may further include a fixing trench 117 surrounding the first chamber 111, in which the fixing trench 117 may be disposed on one end of the first chamber 111, and the end is far away from the first opening 115.

Figure 2B:
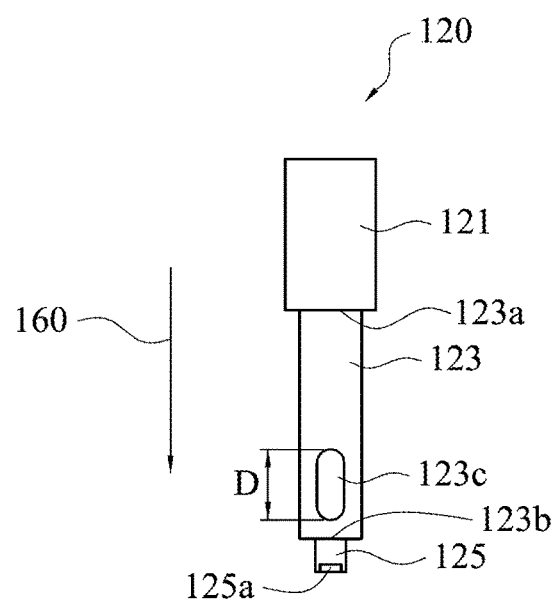
FIG. 2B is a schematic cross-sectional view of a stretchable component of a packaging unit for liquid sample loading devices according to one embodiment of the present invention.

Referring to FIG. 2B, FIG. 2B is a schematic cross-sectional view of a stretchable component of a packaging unit for liquid sample loading devices according to one embodiment of the present invention. As shown in FIG. 2B, the stretchable component 120 includes a joint piece 121, a stretchable piece 123 and a first holding element 125 for holding a first liquid sample loading device (not shown). The joint piece 121 has a first external thread (not shown) matching the first internal thread in the first chamber 111, thereby connecting the stretchable component 120 to the rotating component 110. The stretchable piece 123 has a first end 123a and a second end 123b oppositely disposed to the first end 123a, in which the joint piece 121 is fixed to the first end 123a, a portion of the stretchable piece 123 near the second end 123b has a slide track 123c, and the slide track 123c is disposed along a longitudinal direction 160. The first holding element 125 is fixed to the second end 123b. In one embodiment, the first holding element 125 further has a groove 125a to hold the first liquid sample loading device thereon. In other embodiment, the slide track 123c may have a length D.

Furthermore, the stretchable component 120 may be pushed out from the first accommodation space S1 by the first external thread, the first internal thread and a first fixing pillar 133 (shown in FIG. 20) mentioned later.

Figure 2C:
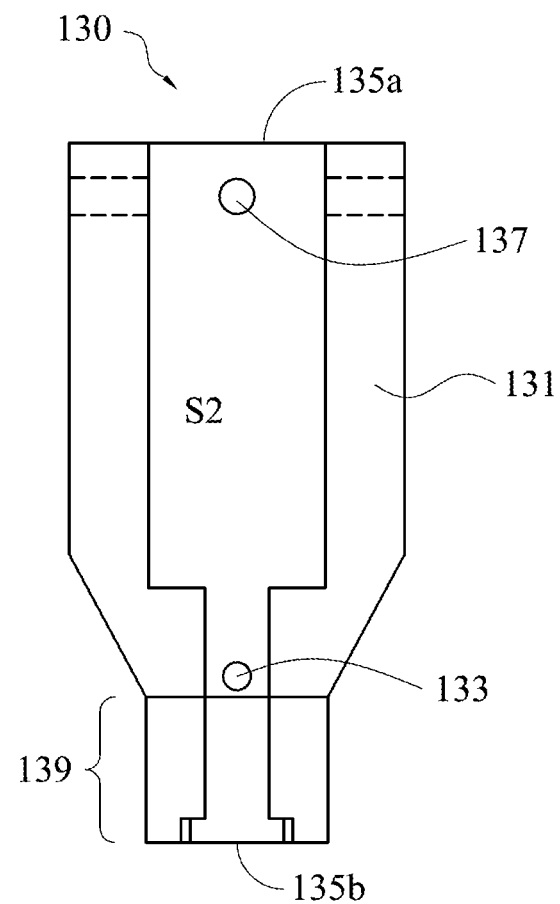
FIG. 2C is a schematic cross-sectional view of a casing of a packaging unit for liquid sample loading devices according to one embodiment of the present invention.

Referring to FIG. 2C, FIG. 2C is a schematic cross-sectional view of a casing of a packaging unit for liquid sample loading devices according to one embodiment of the present invention. As shown in FIG. 2C, the casing 130 includes a second chamber 131 and a first pillar 133, in which the second chamber 131 includes a second accommodation space S2, a second opening 135a and a third opening 135b oppositely disposed to the second opening 135a. A second internal thread (not shown) is disposed in the third opening 135b. The first fixing pillar 133 is close to the third opening 135b, in which the first fixing pillar 133 passes through one side of the casing 130, and slidingly arranged in the slide track 123c (as shown in FIG. 2B).

In one embodiment, the casing 130 may further include a plurality of second pillars 137, which are symmetrically supported on the fixing trench 117 of the rotating component 110. With the second fixing pillars 137 effectively fixing the rotating component 110, a shift of the liquid sample loading device due to swing during a packaging process may be avoided. In a preferable embodiment, the casing 130 may include 4 second fixing pillars 137, but the scope of the present invention is not limited to this.

In one embodiment, the casing 130 may include a transparent observing region 139 disposed near the third opening 135b of the casing 130, so as to observe the packaging process of the liquid sample loading devices.

Figure 2D:
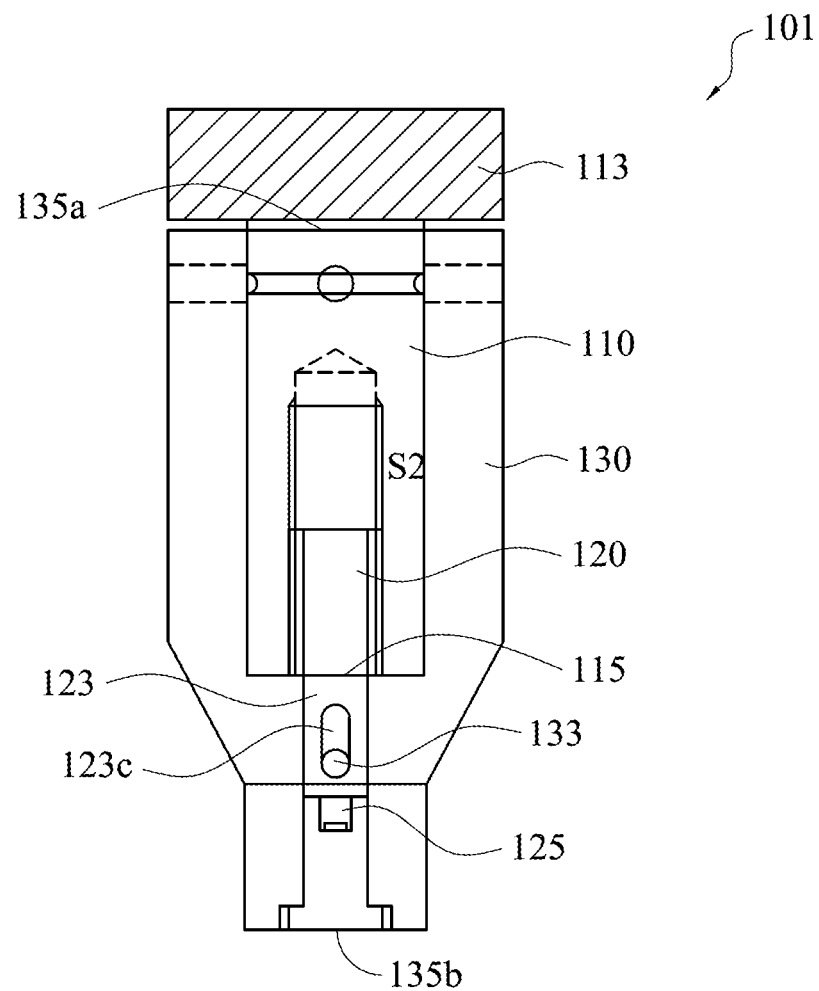
FIG. 2D is a schematic cross-sectional view of an upper jig of a packaging unit for liquid sample loading devices according to one embodiment of the present invention.

Referring to FIG. 2D, FIG. 2D is a schematic cross-sectional view of an upper jig of a packaging unit for liquid sample loading devices according to one embodiment of the present invention. In one embodiment, the upper jig 101 may be obtained by assembling the rotating component 110, the stretchable component 120 and the casing 130, and a structure of the upper jig 101 is shown in FIG. 2D. As shown in FIG. 2D, the first holding element 125 is located near the third opening 135b, and the first fixing pillar 133 is located over the first holding element 125 and slidingly arranged in the slide track 123c. The first holding element 125 and at least one portion of the stretchable piece 123 protrude from the first opening 115, and the rotating component 110 and the stretchable component 120 may be disposed in the second accommodation space S2. In some embodiment, the holder 113 may protrude from the second opening 135a.

Figure 3:
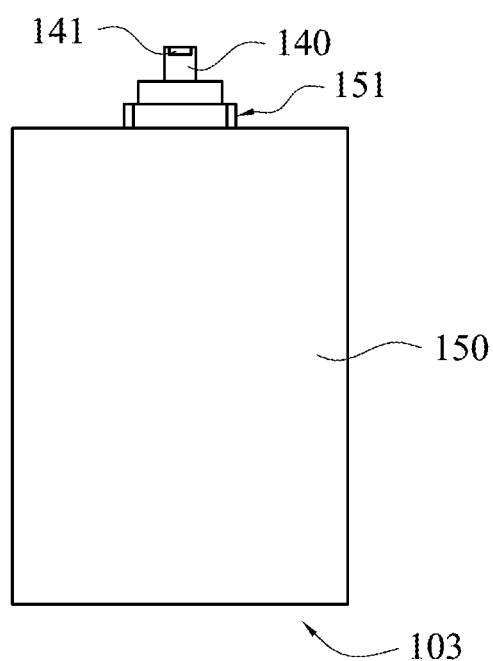
FIG. 3 is a schematic cross-sectional view of a bottom jig of a packaging unit for liquid sample loading devices according to one embodiment of the present invention.

Referring to FIG. 3, FIG. 3 is a schematic cross-sectional view of a bottom jig of a packaging unit for liquid sample loading devices according to one embodiment of the present invention. As shown in FIG. 3, the bottom jig 103 includes the second holding element 140 for holding the second liquid sample loading device (not shown) and the base 150, in which the base 150 is disposed under the second holding element 140. A second external thread (not shown) is disposed on an outer wall 151 of a portion of the base 150, in which the portion is under the second holding element 140. The second external thread (not shown) matches the second internal thread of the casing 130 so that the first holding element 125 and the second holding element 140 may be oppositely disposed. In one embodiment, the second holding element 140 may include a groove 141 to hold the second liquid sample loading device.

In one embodiment, the first holding element 125 and the second holding element 140 may respectively have the same diameter. Furthermore, the diameter is consistent with a diameter of a common liquid sample loading device, for example, the diameter may be 3 mm. In other embodiment, the first holding element 125 and the second holding element 140 may have different diameters.

Figure 4:
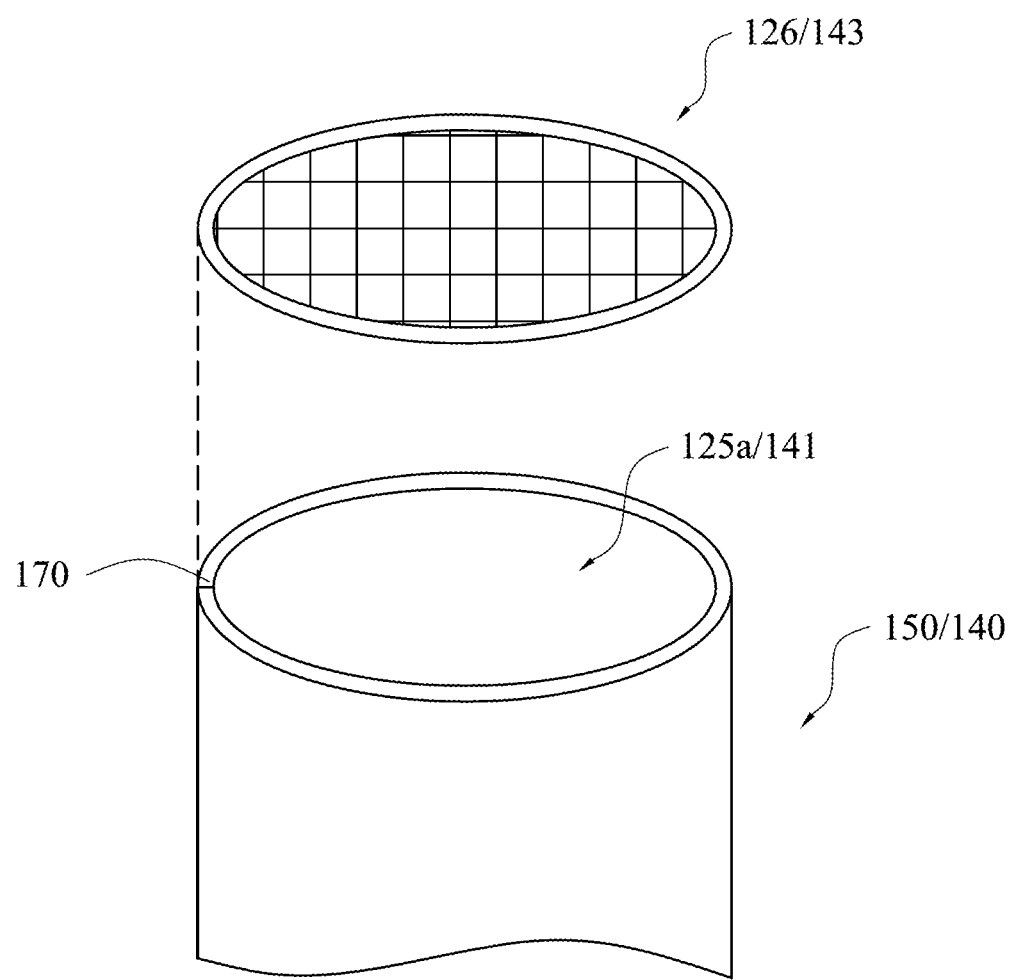
FIG. 4 is a schematic pictorial drawing of holding elements with liquid sample loading devices according to one embodiment of the present invention.

Referring to FIG. 4, FIG. 4 is a schematic pictorial drawing of the holding elements with the liquid sample loading devices according to one embodiment of the present invention. It is noted that the first holding element 125 and the second holding element 140 may have the same arrangement, and thus FIG. 4 illustrates only one holding element. In one embodiment, the first holding element 125 and the second holding element 140 may respectively have an anchor point 170 to align with the first liquid sample loading devices 126 and second liquid sample loading devices 143. To be specific, one of a longitudinal axis and a horizontal axis of the liquid sample loading devices 126/143 may be aligned with the anchor point 170, and thus two liquid sample loading devices 126 and 143 in the first holding element 125 and the second holding element 140 may be respectively fixed in the same orientation, and the two liquid sample loading devices 126 and 143 are self-aligned.

A method of packaging the liquid sample loading devices using the packaging unit of the present invention is described in detailed by the packaging unit 100 of FIG. 1 to FIG. 4. In one embodiment, the first liquid sample loading device 126 is aligned with the anchor point 170 of the first holding element 125, and the first liquid sample loading device 126 is fixed on the groove 125a of the first holding element 125 by a small amount of an adhesive. In addition, a small amount of the adhesive is also applied to a side of the first liquid sample loading device 126 that is not contacted with the first holding element 125. Similarly, the second liquid sample loading device 143 is aligned with the anchor point 170 of the second holding element 140, and the second liquid sample loading device 143 is fixed on the groove 141 of the second holding element 140 by a small amount of the adhesive. Additionally, a small amount of the adhesive is also applied to a side of the second liquid sample loading device 143 that is not contacted with the second holding element 140.

Next, a sample to be detected is added into the first liquid sample loading device 126 on the first holding element 125 or the second liquid sample loading device 143 on the second holding element 140. Then, the upper jig 101 is connected to the bottom jig 103 by engaging the second internal thread of the casing 130 with the second external thread of the base 150. Afterwards, the rotating component 110 is rotated through the holder 113 to push out the stretchable component 120 from the first accommodation space S1 (as shown in FIG. 2A), such that the first holding element 125 and the second holding element 140 contacts each other, and the first liquid sample loading device 126 of the first holding element 125 and the second liquid sample loading device 143 of the second holding element 140 are then adhered and packaged. The packaged liquid sample loading devices are taken out from the packaging unit 100 and detected by an electronic microscope.

It is noted that the slide track 123c of the stretchable piece 123 and the first fixing pillar 133 slidingly arranged in the slide track 123c of the packaging unit of the present invention restrict movement of the stretchable component 120 along a radial direction. Therefore, the stretchable component 120 does not rotate with the rotating component 110, and the stretchable component 120 moves linearly along the longitudinal direction 170. In addition, a moving distance of the stretchable component 120 is limited to the length D (as shown in FIG. 2B) of the slide track 123c, and the length D is designed such that the first holding element 125 and the second holding element 140 of the assembled packaging unit 100 contacts with each other, so as to package the liquid sample loading devices.

Using the packaging unit for the liquid sample loading devices applied in the electron microscope and the packaging method of the present invention, the liquid sample loading devices may be easily, rapidly, precisely and stably aligned and packaged by an engagement of screw threads of the upper jig and the bottom jig, limited rotation of the stretchable component by the fixing pillar, and the slide track with the specific length of the packaging unit. Therefore, efficiency and a yield of packaging the liquid sample loading devices are improved. Accordingly, the packaging unit for the liquid sample loading devices may directly package the liquid sample loading devices holding a liquid sample with high fluidity or low fluidity (e.g. an emulsion or a cream), and the liquid sample maintains its original state.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A packaging unit for liquid sample loading devices applied in an electron microscope, wherein the packaging unit comprises:
    an upper jig, comprising:
        a rotating component, comprising a first chamber, wherein the first chamber has a first accommodation space and a first opening, and a first internal thread is disposed in the first chamber;
        a stretchable component, disposed in the first accommodation space, and the stretchable component comprising:
            a joint piece having a first external thread, wherein the first external thread matches the first internal thread, so as to movably arrange the stretchable component in the first chamber;
            a stretchable piece having one end and the other end oppositely disposed to the end, wherein the end is fixed to the joint piece, a portion of the stretchable piece near the other end has a slide track, and the slide track is disposed along a longitudinal direction; and
            a first holding element for holding a first liquid sample loading device, wherein the first holding element is fixed to the other end of the stretchable piece, and the first holding element and at least one portion of the stretchable piece protrude from the first opening; and
    a casing, comprising:
        a second chamber, comprising:
            a second accommodation space in which the rotating component and the stretchable component are disposed; and
            a second opening and a third opening oppositely disposed to the second opening, wherein a second internal thread is disposed in the third opening, and the first holding element is close to the third opening; and
        a first fixing pillar near the third opening and located above the first holding element, wherein the first fixing pillar passes through a side of the casing and is slidingly arranged in the slide track;
    a bottom jig, comprising a base and a second holding element for holding a second liquid sample loading device, wherein the second holding element is disposed above the base,
    wherein a second external thread is disposed on an outer wall of the base under the second holding element, and the second internal thread matches the second external thread so that the first holding element and the second holding element are oppositely disposed.

2. The packaging unit of claim 1, wherein the first holding element and the second holding element respectively have a groove to hold the first liquid sample loading device and the second liquid sample loading device thereon.

3. The packaging unit of claim 1, wherein the first holding element and the second holding element respectively have an anchor point aligned with the first liquid sample loading device and the second liquid sample loading device.

4. The packaging unit of claim 1, wherein the rotating component further comprises a fixing trench surrounding the first chamber and disposed on one end of the first chamber far away from the first opening.

5. The packaging unit of claim 4, wherein the second opening of the casing comprises a plurality of second fixing pillars, and the second pillars are symmetrically supported on the fixing trench.

6. The packaging unit of claim 1, wherein the casing further comprises a transparent observing region near the third opening of the casing.

7. The packaging unit of claim 1, wherein the rotating component further comprises a holder protruding from the second opening.

8. A packaging method using a packaging unit of claim 1, wherein the method comprises:
- adhering a first liquid sample loading device to a groove of a first holding element;
- adhering a second liquid sample loading device to a groove of a second holding element;
- adding a liquid sample into the first liquid sample loading device or the second liquid sample loading device;
- connecting an upper jig with a bottom jig by engaging an internal thread of a casing with an external thread of a base;
- rotating a rotating component to push out a stretchable component from an accommodation space; and
- contacting the first liquid sample loading device with the second liquid sample loading device, thereby adhering the first liquid sample loading device to the second liquid sample loading device.

9. The method of claim 8, wherein before the liquid sample is added, the method further comprises applying a small amount of an adhesive to a side of the first liquid sample loading device that is not contacted with the first holding element.

10. The method of claim 9, wherein before the liquid sample is added, the method further comprises applying a small amount of the adhesive to a side of the second liquid sample loading device that is not contacted with the second holding element.

11. The method of claim 8, wherein before adhering the first liquid sample loading device to the groove of the first holding element, the method further comprises aligning the first liquid sample loading device to an anchor point of the first holding element.

12. The method of claim 8, wherein before adhering the second liquid sample loading device to the groove of the second holding element, the method further comprises aligning the second liquid sample loading device to an anchor point of the second holding element.

13. The method of claim 8, wherein the rotating component is rotated by rotating a holder.

14. The method of claim 8, wherein the stretchable component moves linearly.

15. The method of claim 14, wherein a moving distance of the stretchable component is equal to a length of a slide track.

* * * * *